(12) United States Patent
Brown et al.

(10) Patent No.: US 6,239,238 B1
(45) Date of Patent: May 29, 2001

(54) BIS-PHOSPHINIMINE CATALYST

(75) Inventors: Stephen John Brown; Xiaoliang Gao; Daryll G. Harrison; Ian McKay; Linda Koch; Qinyan Wang; Wei Xu; Rupert Edward von Haken Spence, all of Calgary; Douglas W. Stephan, La Salle, all of (CA)

(73) Assignee: Nova Chemicals (International) S.A. (CH)

( * ) Notice: Subject to any disclaimer, the term of this patent is extended or adjusted under 35 U.S.C. 154(b) by 0 days.

(21) Appl. No.: 09/333,750

(22) Filed: Jun. 15, 1999

(30) Foreign Application Priority Data

Jul. 21, 1998 (CA) .................................................. 2243783

(51) Int. Cl.$^7$ ........................................................ C08F 4/42

(52) U.S. Cl. ........................... 526/161; 526/172; 526/169; 526/901; 526/125.5; 526/348; 502/155

(58) Field of Search .................................... 526/161, 172, 526/169, 901, 125.3, 348; 502/155

(56) References Cited

U.S. PATENT DOCUMENTS

| | | |
|---|---|---|
| 4,542,199 | 9/1985 | Kaminsky et al. . |
| 4,543,399 | 9/1985 | Jenkins, III et al. . |
| 4,752,597 | 6/1988 | Turner . |
| 4,808,561 | 2/1989 | Welborn, Jr. . |
| 5,198,401 | 3/1993 | Turner et al. . |
| 5,352,749 | 10/1994 | De Chellis et al. . |
| 5,648,310 | 7/1997 | Wasserman et al. . |
| 5,672,669 | 9/1997 | Wasserman et al. . |
| 5,674,795 | 10/1997 | Wasserman et al. . |
| 5,965,677 * | 10/1999 | Stephan et al. ...................... 526/129 |
| 6,013,745 * | 10/1999 | McKay et al. ...................... 526/132 |

* cited by examiner

Primary Examiner—David W. Wu
Assistant Examiner—Ling-Siu Choi
(74) Attorney, Agent, or Firm—Kenneth H. Johnson

(57) ABSTRACT

Organometallic complexes having two phosphinimine ligands and at least one activatable ligand are catalyst components for olefin polymerization. Preferred polymerization systems are prepared by combining the organometallic complexes with an ionic activator and/or an alumoxane. Preferred catalyst components contain titanium, zirconium, or hafnium and are activated with an ionic activator to form catalysts for ethylene polymerization.

5 Claims, No Drawings

BIS-PHOSPHINIMINE CATALYST

FIELD OF THE INVENTION

This invention relates to an olefin polymerization catalyst component which is an organometallic complex having two phosphinimine ligands and at least one activatable ligand. The catalyst component is further characterized by the absence of any cyclopentadienyl ligand.

BACKGROUND OF THE INVENTION

Certain "metallocenes" (especially bis-cyclopentadienyl complexes of group 4 metals) are highly productive catalysts for olefin polymerization when used in combination with an appropriate activator (see, for example, U.S. Pat. No. 4,542,199 (Sinn et al) and U.S. Pat. No. 5,198,401 (Hlatky and Turner).

Olefin polymerization catalysts having one cyclopentadienyl ligand and one phosphinimine ligand are disclosed in a commonly assigned patent application (Stephan et al).

We have now discovered a family of highly active olefin polymerization catalysts which do not contain a cyclopentadienyl ligand.

SUMMARY OF THE INVENTION

The present invention provides a catalyst component for olefin polymerization which is an unbridged bis-phosphinimine complex defined by the formula:

$$(Pl)_2-M-L_n$$

wherein M is a metal selected from group 3-10 metals; each PI is independently a phosphinimine ligand defined by the formula:

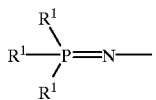

wherein each $R^1$ is independently selected from the group consisting of (a) a hydrogen atom, (b) a halogen atom, (c) $C_{1-20}$ hydrocarbyl radicals which are i) unsubstituted or ii) further substituted by a halogen atom alkoxy radical, (e) a $C_{6-10}$ aryl or aryloxy radical, (f) an amido radical (which may be substituted), (g) a silyl radical of the formula:

wherein each $R^2$ is independently selected from the group consisting of hydrogen, a $C_{1-8}$ alkyl or alkoxy radical, $C_{6-10}$ aryl or aryloxy radicals, and (h) a germanyl radical of the formula:

wherein $R^2$ is as defined above; L is an activatable ligand; n is 1, 2 or 3 depending upon the valence of M with the proviso that L is not a cyclopentadienyl, indenyl or fluorenyl ligand.

DETAILED DESCRIPTION

1. Description of Catalyst Component

The catalyst component of this invention is unbridged. The term "unbridged" is meant to convey its conventional meaning, namely that there is not a bridging group which connects the phosphinimine ligands with formal bonds. (By contrast, many metallocene catalysts having two cyclopentadienyl-type ligands are "bridged" with, for example, a dimethyl silyl "bridge" in which the silicon atom is formally bonded to both of the cyclopentadienyl ligands). "Unbridged" catalyst components are typically less expensive to synthesize than the corresponding bridged analogues.

1.1 Metals

The catalyst component of this invention is an organometallic complex of a group 3, 4, 5, 6, 7, 8, 9 or 10 metal (where the numbers refer to columns in the Periodic Table of the Elements using IUPAC nomenclature). The preferred metals are selected from groups 4 and 5, especially titanium, hafnium, zirconium or vanadium.

1.2 Phosphinimine Ligand

The catalyst component of this invention must contain a phosphinimine ligand which is covalently bonded to the metal. This ligand is defined by the formula:

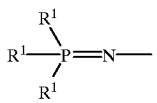

wherein each $R^1$ is independently selected from the group consisting of a hydrogen atom, a halogen atom, $C_{1-20}$ hydrocarbyl radicals which are are i) unsubstituted or ii) further substituted by a halogen atom radical, a $C_{6-10}$ aryl or aryloxy radical, an amido radical, a silyl radical of the formula:

wherein each $R^2$ is independently selected from the group consisting of hydrogen, a $C_{1-8}$ alkyl or alkoxy radical, $C_{6-10}$ aryl or aryloxy radicals, and a germanyl radical of the formula:

wherein $R^2$ is as defined above.

The preferred phosphinimines are those in which each $R^1$ is a hydrocarbyl radical. A particularly preferred phosphinimine is tri-(tertiary butyl) phosphinimine (i.e. where each $R^1$ is a tertiary butyl group).

1.3 Activatable Ligand

The term "activatable ligand" refers to a ligand which may be activated by a cocatalyst (also known as an "activator") to facilitate olefin polymerization. Exemplary activatable ligands are independently selected from the group consisting of a hydrogen atom, a halogen atom, a $C_{1-10}$ hydrocarbyl radical, a $C_{1-10}$ alkoxy radical, a $C_{5-10}$ aryl oxide radical; each of which said hydrocarbyl, alkoxy, and aryl oxide radicals may be unsubstituted by or further substituted by a halogen atom, a $C_{1-8}$ alkyl radical, a $C_{1-8}$ alkoxy radical, a $C_{6-10}$ aryl or aryl oxy radical, an amido radical which is unsubstituted or substituted by up to two $C_{1-8}$ alkyl radicals; a phosphido radical which is unsubstituted or substituted by up to two $C_{1-8}$ alkyl radicals.

The activatable ligands must not be cyclopentadienyl ligands (or related ligands such as indenyl or fluorenyl).

The number of activatable ligands depends upon the valency of the metal and the valency of the activatable ligand. The preferred catalyst metals are group 4 metals in their highest oxidation state (i.e. 4+) and the preferred activatable ligands are monoanionic. Thus, the preferred catalyst components contain two phosphinimine ligands and two (monoanionic) activatable ligands bonded to the group 4 metal. In some instances, the metal of the catalyst component may not be in the highest oxidation state. For example, a titanium (III) component would contain only one activatable ligand.

2. Description of Activators (or "Cocatalysts")

The catalyst components described in part 1 above are used in combination with an "activator" (which may also be referred to by a person skilled in the art as a "cocatalyst") to form an active catalyst system for olefin polymerization. Simple aluminum alkyls and alkoxides may provide comparatively weak cocatalytic activity under certain mild polymerization conditions. However, the preferred activators are alumoxanes and so-called ionic activators, as described below.

2.1 Alumoxanes

The alumoxane activator may be of the formula:

$(R^4)_2AlO(R^4AlO)_mAl(R^4)_2$ wherein each $R^4$ is independently selected from the group consisting of $C_{1-20}$ hydrocarbyl radicals and m is from 0 to 50, preferably $R^4$ is a $C_{1-4}$ alkyl radical and m is from 5 to 30. Methylalumoxane (or "MAO") is the preferred alumoxane.

Alumoxanes are well known as activators for metallocene-type catalysts.

Activation with alumoxane generally requires a molar ratio of aluminum in the activator to (group 4) metal in the catalyst from 20:1 to 1000:1. Preferred ratios are from 50:1 to 250:1.

2.2 Ionic Activators

Ionic activators are also well known for metallocene catalysts. See, for example, U.S. Pat. No. 5,198,401 (Hlatky and Turner). These compounds may be selected from the group consisting of:

(i) compounds of the formula $[R^5]^+[B(R^7)_4]^-$ wherein B is a boron atom, $R^5$ is a cyclic $C_{5-7}$ aromatic cation or a triphenyl methyl cation and each $R^7$ is independently selected from the group consisting of phenyl radicals which are unsubstituted or substituted with from 3 to 5 substituents selected from the group consisting of a fluorine atom, a $C_{1-4}$ alkyl or alkoxy radical which is unsubstituted or substituted by a fluorine atom; and a silyl radical of the formula —Si—$(R^9)_3$; wherein each $R^9$ is independently selected from the group consisting of a hydrogen atom and a $C_{1-4}$ alkyl radical; and (ii) compounds of the formula $[(R^8)_tZH]^+[B(R^7)_4]^-$ wherein B is a boron atom, H is a hydrogen atom, Z is a nitrogen atom or phosphorus atom, t is 2 or 3 and $R^8$ is selected from the group consisting of $C_{1-8}$ alkyl radicals, a phenyl radical which is unsubstituted or substituted by up to three $C_{1-4}$ alkyl radicals, or one $R^8$ taken together with the nitrogen atom may form an anilinium radical and $R^7$ is as defined above; and (iii) compounds of the formula $B(R^7)_3$ wherein $R^7$ is as defined above.

In the above compounds preferably $R^7$ is a pentafluorophenyl radical, and $R_5$ is a triphenylmethyl cation, Z is a nitrogen atom and $R^8$ is a $C_{1-4}$ alkyl radical or $R_8$ taken together with the nitrogen atom forms an anilinium radical which is substituted by two $C_{1-4}$ alkyl radicals.

The "ionic activator" may abstract one or more activatable ligands so as to ionize the catalyst center into a cation but not to covalently bond with the catalyst and to provide sufficient distance between the catalyst and the ionizing activator to permit a polymerizable olefin to enter the resulting active site.

Examples of ionic activators include:
triethylammonium tetra(phenyl)boron,
tripropylammonium tetra(phenyl)boron,
tri(n-butyl)ammonium tetra(phenyl)boron,
trimethylammonium tetra(p-tolyl)boron,
trimethylammonium tetra(o-tolyl)boron,
tributylammonium tetra(pentafluorophenyl)boron,
tripropylammonium tetra(o,p-dimethylphenyl)boron,
tributylammonium tetra(m,m-dimethylphenyl)boron,
tributylammonium tetra(p-trifluoromethylphenyl)boron,
tributylammonium tetra(pentafluorophenyl)boron,
tri(n-butyl)ammonium tetra(o-tolyl)boron,
N,N-dimethylanilinium tetra(phenyl)boron,
N,N-diethylanilinium tetra(phenyl)boron,
N,N-diethylanilinium tetra(phenyl)n-butylboron,
N,N-2,4,6-pentamethylanilinium tetra(phenyl)boron,
di-(isopropyl)ammonium tetra(pentafluorophenyl)boron,
dicyclohexylammonium tetra(phenyl)boron,
triphenylphosphonium tetra(phenyl)boron,
tri(methylphenyl)phosphonium tetra(phenyl)boron,
tri(dimethylphenyl)phosphonium tetra(phenyl)boron,
tropillium tetrakispentafluorophenyl borate,
triphenylmethylium tetrakispentafluorophenyl borate,
benzene (diazonium) tetrakispentafluorophenyl borate,
tropillium phenyltrispentafluorophenyl borate,
triphenylmethylium phenyltrispentafluorophenyl borate,
benzene (diazonium) phenyltrispentafluorophenyl borate,
tropillium tetrakis (2,3,5,6-tetrafluorophenyl) borate,
triphenylmethylium tetrakis (2,3,5,6-tetrafluorophenyl) borate,
benzene (diazonium) tetrakis (3,4,5-trifluorophenyl) borate,
tropillium tetrakis (3,4,5-trifluorophenyl) borate,
benzene (diazonium) tetrakis (3,4,5-trifluorophenyl) borate,
tropillium tetrakis (1,2,2-trifluoroethenyl) borate,
triphenylmethylium tetrakis (1,2,2-trifluoroethenyl) borate,
benzene (diazonium) tetrakis (1,2,2-trifluoroethenyl) borate,
tropillium tetrakis (2,3,4,5-tetrafluorophenyl) borate,
triphenylmethylium tetrakis (2,3,4,5-tetrafluorophenyl) borate, and
benzene (diazonium) tetrakis (2,3,4,5-tetrafluorophenyl) borate.

Readily commercially available ionic activators include: N,N-dimethylaniliumtetrakispentafluorophenyl borate; triphenylmethylium tetrakispentafluorophenyl borate; and trispentafluorophenyl borane.

3. Homogeneous or Heterogeneous Catalyst

The catalyst system of this invention may be used in a homogeneous form in solution polymerization (where the term "homogeneous" means that the catalyst and cocatalyst/activator are soluble in, or miscible with, the polymerization solvent). However, when the catalyst is employed in a slurry or gas phase polymerization, it is highly preferred to use the catalyst in a heterogeneous or "supported form". It is also highly preferred that the catalyst does not cause reactor fouling. The art of preparing heterogeneous catalysts which do not lead to reactor fouling is not adequately understood, though it is generally accepted that the catalytic material should be very well anchored to the support so as to reduce the incidence of fouling resulting from the deposition of catalyst or cocatalyst which has dissociated from the support.

In general, heterogeneous catalysts may be grouped into three main categories:

3.1. Unsupported Alumoxane/Catalyst Mixtures

These catalysts may be easily prepared by evaporating the solvent or diluent from a liquid mixture of an alumoxane and the catalyst component. The resulting product is a solid at room temperature due to the comparatively high molecular weight of the alumoxane. There are two disadvantages to this approach, namely cost (i.e. alumoxanes are comparatively expensive—and the alumoxane is used as an expensive "support" material) and "reaction continuity/fouling" (i.e. the alumoxane may partially melt under polymerization conditions, leading to reactor instability/fouling). U.S. Pat. No. 4,752,597 (Turner, to Exxon) illustrates this approach for the preparation of a heterogeneous catalyst.

3.2. Metal Oxide Supported Catalysts

These catalysts are prepared by depositing the catalyst component and a cocatalyst on a very porous metal oxide support. The catalyst and cocatalyst are substantially contained within the pore structure of the metal oxide particle. This means that a comparatively large metal oxide particle is used (typically particle size of from 40 to 80 microns). The preparation of this type of supported catalyst is described in U.S. Pat. No. 4,808,561 (Welborn, to Exxon).

3.3. Filled/Spray Dried Catalysts

This method of catalyst preparation is also well known. For example, U.S. Pat. Nos. 5,648,310; 5,674,795 and 5,672,669 (all to Union Carbide) teach the preparation of a heterogeneous catalyst by spray drying a mixture which contains a metallocene catalyst, an alumoxane cocatalyst and a "filler" which is characterized by having a very small particle size (less than one micron) and by being unreactive with the catalyst and cocatalyst. The examples illustrate the use of very fine particle size "fumed" silica which has been treated to reduce the concentration of surface hydroxyls. The resulting catalysts exhibit good productivity. Moreover, they offer the potential to provide a catalyst which is not prone to "hot spots" (as the catalyst may be evenly distributed, at low concentration, throughout the heterogeneous matrix). However, these catalysts suffer from the potential disadvantage of being very friable because they are prepared with a fine, "inert" filler material which does not react with/anchor to the catalyst or cocatalyst.

Friable catalyst particles lead to the formation of "fines" in the polyethylene product, and may also aggravate reactor fouling problems.

An alternative approach is the preparation of spray dried catalysts using a hydrotalcite as a "reactive" filler (as opposed to the unreactive filler described in the above-mentioned USP to Union Carbide). This method of catalyst preparation is described in more detail in a commonly assigned patent application. Either approach is suitable for use with the catalysts of this invention.

4. Polymerization Processes

The catalysts of this invention are suitable for use in any conventional olefin polymerization process, such as the so-called "gas phase", "slurry", "high pressure" or "solution" polymerization processes.

The use of a heterogeneous catalyst is preferred for gas phase and slurry processes whereas a homogeneous catalyst is preferred for the solution process.

The polymerization process according to this invention uses ethylene and may include other monomers which are copolymerizable therewith such as other alpha olefins (having from three to ten carbon atoms, preferably butene, hexene or octene) and, under certain conditions, dienes such as hexadiene isomers, vinyl aromatic monomers such as styrene or cyclic olefin monomers such as norbornene.

The present invention may also be used to prepare elastomeric co- and terpolymers of ethylene, propylene and optionally one or more diene monomers. Generally, such elastomeric polymers will contain about 50 to abut 75 weight % ethylene, preferably about 50 to 60 weight % ethylene and correspondingly from 50 to 25% of propylene. A portion of the monomers, typically the propylene monomer, may be replaced by a conjugated diolefin. The diolefin may be present in amounts up to 10 weight % of the polymer although typically is present in amounts from about 3 to 5 weight %. The resulting polymer may have a composition comprising from 40 to 75 weight % of ethylene, from 50 to 15 weight % of propylene and up to 10 weight % of a diene monomer to provide 100 weight % of the polymer. Preferred but not limiting examples of the dienes are dicyclopentadiene, 1,4-hexadiene, 5-methylene-2-norbornene, 5-ethylidene-2-norbornene and 5-vinyl-2-norbornene. Particularly preferred dienes are 5-ethylidene-2-norbornene and 1,4-hexadiene.

The polyethylene polymers which may be prepared in accordance with the present invention typically comprise not less than 60, preferably not less than 70 weight % of ethylene and the balance one or more $C_{4-10}$ alpha olefins, preferably selected from the group consisting of 1-butene, 1-hexene and 1-octene. The polyethylene prepared in accordance with the present invention may be linear low density polyethylene having density from about 0.910 to 0.935 g/cc. The present invention might also be useful to prepare polyethylene having a density below 0.910 g/cc—the so-called very low and ultra low density polyethylenes.

The most preferred polymerization process of this invention encompasses the use of the novel catalysts (together with a cocatalyst) in a medium pressure solution process. As used herein, the term "medium pressure solution process" refers to a polymerization carried out in a solvent for the polymer at an operating temperature from 100 to 320° C. (especially from 120 to 220° C.) and a total pressure of from 3 to 35 mega Pascals. Hydrogen may be used in this process to control (reduce) molecular weight. Optimal catalyst and cocatalyst concentrations are affected by such variables as temperature and monomer concentration but may be quickly optimized by non-inventive tests.

Further details concerning the medium pressure polymerization process are well known to those skilled in the art and widely described in the open and patent literature.

The catalyst of this invention may also be used in a slurry polymerization process or a gas phase polymerization process.

The typical slurry polymerization process uses total reactor pressures of up to about 50 bars and reactor temperature of up to about 200° C. The process employs a liquid medium (e.g. an aromatic such as toluene or an alkane such as hexane, propane or isobutane) in which the polymerization takes place. This results in a suspension of solid polymer particles in the medium. Loop reactors are widely used in slurry processes. Detailed descriptions of slurry polymerization processes are widely reported in the open and patent literature.

In general, a fluidized bed gas phase polymerization reactor employs a "bed" of polymer and catalyst which is fluidized by a flow of monomer which is at least partially gaseous. Heat is generated by the enthalpy of polymerization of the monomer flowing through the bed. Unreacted monomer exits the fluidized bed and is contacted with a cooling system to remove this heat. The cooled monomer is then re-circulated through the polymerization zone together with "make-up" monomer to replace that which was polymerized on the previous pass. As will be appreciated by those skilled in the art, the "fluidized" nature of the polymerization bed helps to evenly distribute/mix the heat of reaction and thereby minimize the formation of localized temperature gradients (or "hot spots"). Nonetheless, it is essential that the heat of reaction be properly removed so as to avoid softening or melting of the polymer (and the resultant and highly undesirable - "reactor chunks"). The obvious way to maintain good mixing and cooling is to have a very high monomer flow through the bed. However, extremely high monomer flow causes undesirable polymer entrainment.

An alternative (and preferable) approach to high monomer flow is the use of an inert condensable fluid which will boil in the fluidized bed (when exposed to the enthalpy of polymerization), then exit the fluidized bed as a gas, then come into contact with a cooling element which condenses the inert fluid. The condensed, cooled fluid is then returned to the polymerization zone and the boiling/condensing cycle is repeated.

The above-described use of a condensable fluid additive in a gas phase polymerization is often referred to by those skilled in the art as "condensed mode operation" and is described in additional detail in U.S. Pat. No. 4,543,399 and U.S. Pat. No. 5,352,749. As noted in the '399 reference, it is permissible to use alkanes such as butane, pentanes or hexanes as the condensable fluid and the amount of such condensed fluid preferably does not exceed about 20 weight per cent of the gas phase.

Other reaction conditions for the polymerization of ethylene which are reported in the '399 reference are:

Preferred Polymerization Temperatures: about 75° C. to about 115° C. (with the lower temperatures being preferred for lower melting copolymers—especially those having densities of less than 0.915 g/cc—and the higher temperatures being preferred for higher density copolymers and homopolymers); and Pressure: up to about 1000 psi (with a preferred range of from about 100 to 350 psi for olefin polymerization).

The '399 reference teaches that the fluidized bed process is well adapted for the preparation of polyethylene but further notes that other monomers may be employed—as is the case in the process of this invention.

EXAMPLES

The invention will now be illustrated in further detail by way of the following non-limiting examples. For clarity, the Examples have been divided into three parts, namely Part A (Catalyst Component Synthesis), Part B (Solution Polymerization) and Part C (Gas Phase Polymerization).

Polymer Analysis

Gel permeation chromatography ("GPC") analysis was carried out using a commercially available chromatograph (sold under the name Waters 150 GPC) using 1,2,4-trichlorobenzene as the mobile phase at 140° C. The samples were prepared by dissolving the polymer in the mobile phase solvent in an external oven at 0.1% (weight/volume) and were run without filtration. Molecular weights are expressed as polyethylene equivalents with a relative standard deviation of 2.9% and 5.0% for the number average molecular weight (Mn) and weight average molecular weight (Mw), respectively. Melt index (Ml) measurements were conducted according to ASTM method D-1238-82.

Polymer densities were measured using pressed plaques (ASTM method D-1928-90), with a densitometer.

The following abbreviations are used in the Examples:

$^tBu$ =tertiary butyl (e.g. $^tBu_3$=tri-tertiary butyl)

Me=methyl

Et=ethyl $^1H$ NMR=proton nuclear magnetic resonance $^iPr$=isopropyl

Ph=phenyl

Mw=weight average molecular weight

Mn=number average molecular weight

PD=polydispersity (or Mw/Mn)

PE=polyethylene

Cat=catalyst

Hr=hour

M=molar

Part A Catalyst Component Synthesis

A.1 Synthesis of $(^tBu_3PN)(^iPr_3PN)TiCl_2$ $^iPr_3P=N-SiMe_3$ (0.6 g, 2.43 mmol) was added to a toluene solution (~60 mL) of $^tBu_3PNTiCl_3$. The solution was refluxed at 120° C. (bath temperature) for 45 hours and was concentrated to ~3 mL. The product was crystallized at −70° C. after the solution was mixed with heptane (~10 mL). The yield was 0.87 g, 85%. $^1H$ NMR (δ, $C_7D_8$): 1.78 (m, 3H), 1.351 (dd, $J_1$=13.0 Hz, $J_2$=1.2 Hz, 27H), 1.064 (dd, $J_1$=14.8 hz, $J_2$=7.19 Hz, 18H).

A.2 Methylation of $(^tBU_3PN)(^iPr_3PN)TiCl_2$

MeMgBr in diethyl ether (3M, 0.75 mL, 2.2 mmol) was added to a toluene solution (~20 mL) of $(^tBu_3PN)(^iPr_3PN)TiCl_2$ (0.509 g, 1 mmol). The mixture was stirred for 1 hour, the volatiles were stripped off by vacuum pumping and the remaining solid was extracted with hexane (3×15 mL). The hexane extract was pumped to dryness and a crystalline solid was obtained. The identity of the product was proved to be $(^tBU_3PN)_2TiMe_2$. $^1H$ NMR (δ, $C_7D_8$): 1.379 (d, J=12.5 Hz, 54 H), 0.777 (s, 6H). The result was further verified by two independent reactions. The residual solid was treated with $Me_3SiCl$ in ether, pumped to dryness and was extracted with hexane again. The extract was pumped to dryness and the residue was checked with NMR which showed the resonance (doublets of doublet) of $^iPr_3P$ fragment and two other resonances. There was no resonance due to the $^tBu_3PN$ ligand.

A.3 Synthesis of $(^iPr_3PN)_2TiCl_2$ $^iPr_3P=N-SiMe_3$ (0.990 g, 4.0 mmol) was added to a toluene solution (60 mL) of $TiCl_4$ (0.380 g, 2 mmol). The solution was refluxed for 1 hour and a brown solution formed. 25 mg of anhydrous $Na_2SO_4$ (accelerates the reaction) was then added to the solution which was refluxed overnight. A transparent, light blue solution formed. The solution was filtered to remove a slight amount of solid and was pumped to dryness. An almost white solid was obtained (quantitative yield). $^1H$ NMR showed that the product is pure. $^1H$ NMR (δ, $C_7D_8$): 1.80 (m, 6H), 1.06 (dd, $J_1$=14.8 Hz, $J_2$=7.20 Hz, 36 H).

A.4 Synthesis of $(^iPr_3PN)_2TiMe_2$

MeMgBr in diethyl ether (3.0 M, 0.7 mL, 2.0 mmol) was added to a toluene solution (20 mL) of $(^iPr_3PN)_2TiCl_2$ (0.467 g, 1 mmol). The mixture was stirred for about 1 hour and volatiles were removed under vacuum. The residue was extracted with hexane (3×20 mL) and the extract was slowly pumped to dryness. The product was obtained as a white crystalline solid (420 mg, ~100%). $^1H$ NMR (δ, $C_7D_8$): 2.27 (m, 6H), 1.40 (dd, $J_1$=15.3 Hz, $J_2$=7.24 Hz, 36 H), 0.867 (s, 6H).

A.5 Synthesis of bis(tri-t-butylphosphinimine) zirconiumdibenzyl

A solution of tri-t-butylphosphinimine (868 mg, 4 mmol) in toluene (20 mL) was added dropwise to a solution of tetrabenzylzirconium (910 mg, 2 mmol) in toluene (80 mL) at 10° C. The reaction was warmed to room temperature and stirred for five minutes. The toluene was removed in vacuo and the resulting oil dissolved in hexane (30 mL). The solution was filtered and the hexane removed in vacuo to leave an oil that crystallized as a white solid on standing at room temperature for several hours. Yield 1.115 g. The product was pure by $^1H$ NMR spectroscopy except for a small amount of unreacted tri-t-butylphosphinimine. 1 H ($C_7D_8$): 7.17–6.80 (multiplet), 2.23 (s), 1.22 (d, $^3J_{P-H}$ =12.4 Hz).

A.6 Synthesis of bis(tri-t-butylphosphinimine)titanium dichloride

To a solution of titanium tetrachloride (336 mg; 1.77 mmol) in toluene (20 mL) was added solid tri-t-butylphosphinimine-N-trimethylsilyl (1.025 g, 3.55 mmol). The reaction was heated to 110° C. overnight and then the toluene was removed in vacuo. The product was taken up in fresh toluene, filtered and concentrated. The product crystallized out as a pure product. Yield 0.664 g. 1H ($C_7D_8$): 1.33 (d, $J_{P-H}$=12.7 Hz).

A.7 Synthesis of bis(tri-t-butylphosphinimine)titanium Dimethyl

To a slurry of bis(tri-t-butylphosphinimine)titanium dichloride (340 mg; 0.62 mmol) in ether (15 mL) was added MeMgBr (0.7 mL, 3 M, 2.1 mmol) at −78° C. The reaction was stirred at room temperature 20 minutes before the volatiles were removed in vacuo. The product was extracted with hexane, the reaction filtered and the hexane removed to yield a white crystalline solid. Yield 280 mg, 90%. 1 H (C$_7$D$_8$): 1.37(d, J$_{P-H}$=12.5 Hz), 0.77 (s).

Part B Solution Polymerization

Solution polymerizations were completed either in a Solution Batch Reactor ("SBR") or in a continuous reaction. The "SBR" experiments are described in Part B.1 and the continuous experiments in Part B.2.

B.1 SBR Experimental Conditions

The SBR uses a programmable logical control (PLC) system with Wonderware 5.1 software for process control. Ethylene polymerizations were performed in a 500 mL Autoclave Engineers Zipperclave reactor equipped with an air driven stirrer and an automatic temperature control system. All the chemicals were fed into the reactor batchwise except ethylene which was fed on demand.

Typical experimental conditions for screening experiments are tabulated below.

| | |
|---|---|
| Cyclohexane | 216 mL |
| Catalyst Concentration | 200 μmol/L |
| Activator | 210 μmol/L |
| Scavenger | • PMAO-IP 1 mmol/L put into the reactor with 216 mL reaction solvent. |
| | • PMAO-IP 1 mmol/L dissolved in 250 mL of cyclohexane as the scavenger, the solution was stirred for 10 minutes at room temperature, then withdrawn with a canula before the reaction solvent was loaded in |
| Reaction Temperature | 160° C. |
| Reactor Pressure | 140 psig total |
| Stirring Speed | 2000 rpm |
| Comonomer | 10 or 20 mL of octene |

Notes:
1. Table B.1 identifies the borane or borate activator used in each experiment.
2. "PMAO-IP" is a commercially available methylalumoxane.

tor and the catalyst. Because of the low solubility of the catalysts, activators and MAO in cyclohexane, solutions were prepared in purified xylene. The catalyst was activated in situ (in the polymerization reactor) at the reaction temperature in the presence of the monomers. The polymerizations were carried out in cyclohexane at a pressure of 1500 psi. Ethylene was supplied to the reactor by a calibrated thermal mass flow meter and was dissolved in the reaction solvent prior to the polymerization reactor. If comonomer (for example 1-octene) was used it was also premixed with the ethylene before entering the polymerization reactor. Under these conditions the ethylene conversion is a dependent variable controlled by the catalyst concentration, reaction temperature and catalyst activity, etc.

The internal reactor temperature is monitored by a thermocouple in the polymerization medium and can be controlled at the required set point to +/−0.5 C. Downstream of the reactor the pressure was reduced from the reaction pressure (1500 psi) to atmospheric. The solid polymer was then recovered as a slurry in the condensed solvent and was dried by evaporation before analysis.

The ethylene conversion was determined by a dedicated on-line gas chromatograph by reference to propane which was used as an internal standard. The average polymerization rate constant was calculated based on the reactor hold-up time, the catalyst concentration in the reactor and the ethylene conversion and is expressed in l/(mmol*min). Average polymerization rate (kp)=(Q/(100−Q))×(1/[TM])×(1/HUT), where:

Q is the percent ethylene conversion;

[TM] is the catalyst concentration in the reactor expressed in mM; and

HUT is the reactor hold-up time in minutes.

Polymer Analysis

Melt index (MI) measurements were conducted according to ASTM method D-1238-82.

Polymer densities were measured on pressed plaques (ASTM D-1928-90) with a densitometer.

TABLE B.1

| Run # | 1-octene (mL) | Catalyst | Activator | Activity (g PE/mmol {cat} Hr) | Mw (*10$^{-3}$) and PD | Branch/1000 C (density) |
|---|---|---|---|---|---|---|
| 10404 | | Me$_2$Ti(NP$^t$Bu$_3$)$_2$ (1) | [CPh$_3$][B(C$_6$F$_5$)$_4$] | 2430.8 | 114.4 (2.6) | |
| 10402 | | (NP$^t$Bu$_3$)$_2$Zr(CH$_2$Ph)$_2$ (2) | [CPh$_3$][B(C$_6$F$_5$)$_4$] | 377.15 | 1.84 (1.8) | |
| 10406 | 20 | Me$_2$Ti(NP$^t$Bu$_3$)$_2$ (1) | [CPh$_3$][B(C$_6$F$_5$)$_4$] | 2039.8 | 18.7 (5.5) | 57 (0.866) |
| 10413 | 20 | Me$_2$Ti(NP$^t$Bu$_3$)$_2$ (1) | [NHMe$_2$Ph][B(C$_6$F$_5$)$_4$] | 3407.4 | 29.7 (7.0) | 63 (0.886) |
| 10419 | 10 | Me$_2$Ti(NP$^t$Bu$_3$)$_2$ (1) | [NHMe$_2$Ph][B(C$_6$F$_5$)$_4$] | 4672.1 | 60.0 (5.6) | 26.6 |
| 10409 | 20 | Me$_2$Ti(NP$^t$Bu$_3$)$_2$ | B(C$_6$F$_5$)$_3$ | 2784.9 | 25.0 (4.4) | 34.3 (0.886) |

Notes:
(1) Catalyst from Part A, Section A.7
(2) Catalyst from Part A, Section A.5

B.2 Continuous Solution Polymerization

All the polymerization experiments described below were conducted on a continuous solution polymerization reactor. The process is continuous in all feed streams (solvent, monomers and catalyst) and in the removal of product. All feed streams were purified prior to the reactor by contact with various absorption media to remove catalyst killing impurities such as water, oxygen and polar materials as is known to those skilled in the art. All components were stored and manipulated under an atmosphere of purified nitrogen.

All the examples below were conducted in a reactor of 71.5 cc internal volume. In each experiment the volumetric feed to the reactor was kept constant and as a consequence so was the reactor residence time.

The catalyst solutions were pumped to the reactor independently and there was no pre-contact between the activa- Example 1

[($^t$Bu)$_3$PN)]$_2$TiMe$_2$ (from Part A, Section A.7) was added to the reactor at 9.3×10$^{-6}$ mol/l along with Ph$_3$C B(C$_6$F$_5$)$_4$ (Asahi Glass) at B/Ti=1.00 (mol/mol). The reaction temperature was 160° C. and 2.1 gram/min of ethylene was continuously added to the reactor. An ethylene conversion of 99.6% was observed (see Table B.2).

Example 2

[($^t$Bu)$_3$PN)]$_2$TiMe$_2$ (from Part A, Section A.7) was added to the reactor at 9.3×10$^{-6}$ mol/l along with MAO (MMAO-7 Akzo Nobel) at Al/Ti=50 (mol/mol). The reaction temperature was 160° C. and 2.1 gram/min of ethylene was continuously added to the reactor. An ethylene conversion of approximately 10% was observed (see Table B.2).

Example 3

[($^t$Bu)$_3$PN)]$_2$TiMe$_2$ (from Part A, Section A.7) was added to the reactor at 9.3×10$^{-6}$ mol/l along with Ph$_3$C B(C$_6$F$_5$)$_4$ (Asahi Glass) at B/Ti=1.00 (mol/mol). The reaction temperature was 200° C. and 3.8 gram/min of ethylene was continuously added to the reactor. An ethylene conversion of 90.1% was observed (see Table B.2).

Example 4

[($^t$Bu)$_3$PN)]$_2$TiMe$_2$ (from Part A, Section A.7) was added to the reactor at 4.6×10$^{-6}$ mol/l along with Ph$_3$C B(C$_6$F$_5$)$_4$ (Asahi Glass) at B/Ti=0.5 (mol/mol). The reaction temperature was 160° C. and 2.1 gram/min of ethylene was continuously added to the reactor. In addition 1.0 ml/min of 1-octene was also added. An ethylene conversion of 90.4% was observed (see Table B.2).

Example 5

[($^t$Bu)$_3$PN)]$_2$TiMe$_2$ (from Part A, Section A.7) was added to the reactor at 4.6×10$^{-6}$ mol/l along with Ph$_3$C B(C$_6$F$_5$)$_4$ (Asahi Glass) at B/Ti=0.5 (mol/mol). The reaction temperature was 160° C. and 2.1 gram/min of ethylene was continuously added to the reactor. In addition 3.0 ml/min of 1-octene was also added. An ethylene conversion of 88.0% was observed (see Table B.2).

Comparative Example C (C$_5$Me$_5$)$_2$ZrCl$_2$ (Strem) was added to the reactor at 37×10$^{-6}$ mol/l along with MMAO-3 (Akzo-Nobel, Al/Ti=400 mol/mol). The reaction temperature was 160° C. and 2.1 gram/min of ethylene was continuously added to the reactor. An ethylene conversion of 37.4% was observed (see Table B.3).

Comparative Example D rac-Et(ind)$_2$ZrCl$_2$ (purchased from Witco) was added to the reactor at 37×10$^{-6}$ mol/l along with MMAO-3 (Akzo-Nobel, Al/Ti=400 mol/mol). The reaction temperature was 160° C. and 2.1 gram/min of ethylene was continuously added to the reactor. An ethylene conversion of 94.6 % was observed (see Table B.3). Comparative Example E rac-Et (ind)$_2$ZrCl$_2$ (Witco) was added to the reactor at 37×10$^{-6}$ mol/l along with MMAO-3 (Akzo-Nobel, Al/Ti=400 mol/mol). The reaction temperature was 160° C. and 2.1 gram/min of ethylene and 3.25 ml/min of 1-octene was continuously added to the reactor. An ethylene conversion of 94.8% was observed (see Table B.3).

TABLE B.2

| Example | Total Flow to Reactor (ml/min) | Catalyst Concentration (mol/l × 10$^6$) | Ethylene Conversion (%) | Calculated Polymerization Rate (kp) (l/mmol × min) | Polymer Density (g/cc) | Polymer Melt Index | Mn × 10$^{-3}$ | Mw × 10$^{-3}$ |
|---|---|---|---|---|---|---|---|---|
| 1 | 27.0 | 9.3 | 99.6 | 9444 | — | — | — | — |
| 2 | 27.0 | 9.3 | 10 | 4.5 | — | — | — | — |
| 3 | 27.0 | 9.3 | 90.1 | 372 | 0.957 | 3.03 | 25.8 | 51.2 |
| 4 | 27.0 | 4.6 | 90.4 | 767 | 0.917 | 24.9 | 19.8 | 38.4 |
| 5 | 27.0 | 4.6 | 88.0 | 560 | 0.895 | 445 | — | — |

TABLE B.3

| Example | Total Flow to Reactor (ml/min) | Catalyst Concentration (mol/l × 10$^6$) | Ethylene Conversion (%) | Calculated Polymerization Rate (kp) (l/mmol × min) | Polymer Density (g/cc) | Polymer Melt Index | Mn × 10$^{-3}$ | Mw × 10$^{-3}$ |
|---|---|---|---|---|---|---|---|---|
| A$^c$ | 27.0 | 37.0 | 55.5 | 13 | — | 880 | 2.7 | 10.0 |
| B$^c$ | 27.0 | 37.0 | 35.6 | 6 | — | — | 1.8 | 7.5 |
| C$^c$ | 27.0 | 37.0 | 37.4 | 6 | — | 620 | 3.3 | 12.0 |
| D$^c$ | 27.0 | 37.0 | 94.6 | 179 | — | 1300 | 3.9 | 14.0 |
| E$^c$ | 27.0 | 37.0 | 94.8 | 186 | 0.925 | very high | 2.6 | 10.0 |

$^c$Comparative

Comparative Example A (C$_5$Me$_5$)$_2$ZrCl$_2$ (purchased from Strem) was added to the reactor at 37×10$^{-6}$ mol/l along with MMAO-3 (Akzo-Nobel, Al/Ti=400 mol/mol). The reaction temperature was 140° C. and 1.0 gram/min of ethylene was continuously added to the reactor. An ethylene conversion of 55.5% was observed (see Table B.3).

Comparative Example B (C$_5$Me$_5$)$_2$ZrCl$_2$ (Strem) was added to the reactor at 37×10$^{-6}$ mol/l along with MMAO-3 (Akzo-Nobel, Al/Ti=400 mol/mol). The reaction temperature was 160° C. and 1.0 gram/min of ethylene was continuously added to the reactor. An ethylene conversion of 35.6% was observed (see Table B.3).

Part C Gas Phase Polymerization
Catalyst Preparation and Polymerization Testing Using a Semi-Batch, Gas Phase Reactor The catalyst preparation methods described below employ typical techniques for the syntheses and handling of air-sensitive materials. Standard Schlenk and drybox techniques were used in the preparation of the supported catalysts. Solvents were purchased as anhydrous materials and further treated to remove oxygen and polar impurities by contact with a combination of activated alumina, molecular sieves and copper oxide on silica/alumina. Where appropriate, elemental compositions of the supported catalysts were measured by Neutron Activation analysis and a reported accuracy of ±1% (weight basis).

The supported catalysts were prepared by initially supporting MAO on a silica support, followed by deposition of the catalyst component.

All the polymerization experiments described below were conducted using a semi-batch, gas phase polymerization reactor of total internal volume of 2.2 L. Reaction gas mixtures, including separately ethylene or ethylene/butene mixtures, were measured in the reactor on a continuous basis using a calibrated thermal mass flow meter, following passage through purification media as described above. A predetermined mass of the catalyst sample was added to the reactor under the flow of the inlet gas with no pre-contact of the catalyst with any reagent, such as a catalyst activator. The catalyst was activated in situ (in the polymerization reactor) at the reaction temperature in the presence of the monomers, using a metal alkyl complex which has been previously added to the reactor to remove adventitious impurities. Purified and rigorously anhydrous sodium chloride was used as a catalyst dispersing agent.

The internal reactor temperature was monitored by a thermocouple in the polymerization medium and can be controlled at the required set point to ±1.0° C. The duration of the polymerization experiment was one hour. Following the completion of the polymerization experiment, the polymer was separated from the sodium chloride and the yield determined.

Table C illustrates data concerning the Al/transition metal ratios of the supported catalyst, polymer yield and polymer properties.

TABLE C

| Complex | mmol Complex | Support* | mg of Catalyst | Yield g | gPe/g Metal | gPe/g Catalyst | Al/M ratio |
|---|---|---|---|---|---|---|---|
| [N=P(tBu)$_3$]$_2$TiCl$_2$ | 28 mg (0.0508 mmol) | 0.5 | 55 | 0.5 | 1898 | 9.1 | 91.20 |

Notes:
1. Support is silica treated with MAO (purchased from Witco)
2. Ethylene-Butene copolymerization (Co) 4 mol. % 1-Butene
3. Pe = Polyethylene
4. The catalyst is from Part A, Section A.6

What is claimed is:

1. A process for the polymerization of ethylene and optionally, a minor amount of at least one additional alpha olefin having from three to ten carbon atoms, wherein said process is conducted in the presence of: A a catalyst component for olefin polymerization which is an unbridged bis-phosphinimine complex defined by the formula:

(Pl)$_2$—M—L$_n$ wherein M is a group 4 metal; each Pl is independently a phosphinimine ligand defined by the formula:

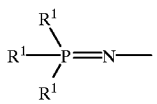

wherein each $R^1$ is independently selected from the group consisting of (a) a hydrogen atom, (b) a halogen atom, (c) $C_{1-20}$ hydrocarbyl radicals which are (i) unsubstituted or (ii) further substituted by a halogen atom, (d) a $C_{1-8}$ alkoxy radical, (e) a $C_{6-10}$ aryl or aryloxy radical, (f) an amido radical, (g) a silyl radical of the formula:

—Si—($R^2$)$_3$ wherein each $R^2$ is independently selected from the group consisting of hydrogen, a $C_{1-8}$ alkyl or alkoxy radical, $C_{6-10}$ aryl and $C_{6-10}$ aryloxy radicals, and (h) a germanyl radical of the formula:

Ge—($R^2$)$_3$ wherein $R^2$ is as defined above; L is an activatable ligand; n is 1, 2 or 3 depending upon the valence of M with the proviso that L is not a cyclopentadienyl, indenyl or fluorenyl ligand; and B an activator.

2. The process according to claim 1 wherein said activator is an ionic activator.

3. The process according to claim 2 where said ionic activator comprises an organometallic boron complex containing one boron atom and at least three perfluorinated phenyl ligands bonded to said boron atom.

4. The process according to claim 1 when undertaken under medium pressure solution polymerization conditions at a temperature of from 100 to 320° C. and a pressure of from 3 to 35 mega Pascals.

5. The process according to claim 4 wherein said metal is titanium (IV); each of said phosphinimine ligand is tri (tertiary-butyl) phosphinimine; and said activator is an ionic activator comprising an organometallic boron complex containing one boron atom and at least three perfluorinated phenyl ligands bonded to said boron atom.

* * * * *